(12) United States Patent
Mennen et al.

(10) Patent No.: US 9,776,957 B2
(45) Date of Patent: Oct. 3, 2017

(54) ZERO EMISSION UREA PROCESS AND PLANT

(75) Inventors: Johannes Henricus Mennen, Meijel (NL); Barbara Cucchiella, Rome (IT)

(73) Assignee: STAMICARBON B.V., Sittard (NL)

( * ) Notice: Subject to any disclaimer, the term of this patent is extended or adjusted under 35 U.S.C. 154(b) by 230 days.

(21) Appl. No.: 14/007,637

(22) PCT Filed: Mar. 30, 2012

(86) PCT No.: PCT/NL2012/050207
§ 371 (c)(1),
(2), (4) Date: Sep. 25, 2013

(87) PCT Pub. No.: WO2012/134288
PCT Pub. Date: Oct. 4, 2012

(65) Prior Publication Data
US 2014/0046094 A1    Feb. 13, 2014

(30) Foreign Application Priority Data

Mar. 31, 2011    (EP) .................................... 11160716

(51) Int. Cl.
*C07C 273/04*    (2006.01)
*B01J 19/24*    (2006.01)

(52) U.S. Cl.
CPC ............. *C07C 273/04* (2013.01); *B01J 19/24* (2013.01)

(58) Field of Classification Search
CPC ............................... B01J 19/24; C07C 273/04
See application file for complete search history.

(56) References Cited

U.S. PATENT DOCUMENTS

| | | | | |
|---|---|---|---|---|
| 2,046,827 A | * | 7/1936 | Lawrence | C07C 273/04 423/403 |
| 2,135,058 A | * | 11/1938 | Spicer | C01B 3/40 423/652 |
| 3,838,193 A | * | 9/1974 | Kajitani | C01B 21/02 423/235 |
| 5,582,656 A | | 12/1996 | Kangas et al. | |
| 5,612,010 A | * | 3/1997 | Pandey | B01D 53/8625 423/239.1 |
| 6,328,941 B1 | * | 12/2001 | Watzenberger | B01D 53/005 423/235 |
| 6,632,846 B2 | * | 10/2003 | Sheppard | C07C 1/0485 423/359 |

FOREIGN PATENT DOCUMENTS

| | | |
|---|---|---|
| CN | 1125965 | 7/1996 |
| CN | 101451711 | 6/2009 |
| GB | 753671 | * 7/1956 |
| WO | WO-95/00674 | 1/1995 |

OTHER PUBLICATIONS

Gevers et al., "Can passivation air in urea plants be minimized through the use of Safurex and consequently improve plant safety?", International Fertilizer Industry Association Technical Conference, Sep. 27, 2002.
International Search Report for PCT/NL2012/050207, mailed Jul. 5, 2012, 3 pages.
Meessen, "The Stamicarbon NEXT Generation Urea Plant," FAI Seminar, Dec. 5, 2009.

* cited by examiner

*Primary Examiner* — Paul A Zucker
*Assistant Examiner* — Mark Luderer
(74) *Attorney, Agent, or Firm* — Morrison & Foerster LLP

(57) ABSTRACT

Disclosed is a method for the production of urea allowing a substantial reduction, even down to zero, of the continuous emission of ammonia conventionally resulting from such a process. According to a preferred embodiment of the invention, the urea-forming reaction from carbon dioxide and ammonia is conducted in a synthesis section that does not require passivation by oxygen. As a result of the absence of oxygen, a hydrogen-rich gas stream results from the synthesis section, that can be used as a fuel in an incinerator. In the incinerator, ammonia-comprising gas streams from the urea production process are combusted.

15 Claims, 2 Drawing Sheets

ZERO EMISSION UREA PROCESS AND PLANT

CROSS-REFERENCE TO RELATED APPLICATIONS

This application is the national phase of PCT application PCT/NL2012/050207 having an international filing date of 30 Mar. 2012, which claims benefit of European application No. 11160716.4, filed 31 Mar. 2011. The contents of the above patent applications are incorporated by reference herein in their entirety.

FIELD OF THE INVENTION

The invention is in the field of reducing the continuous ammonia emission in the production of urea, particularly in a urea melt production process. The invention is also directed to the use of a urea synthesis section that does not require passivation by oxygen in achieving a reduction of ammonia emissions and to urea production facilities in which the hydrogen in the carbon dioxide feedstock is not combusted. The invention also pertains to a urea plant comprising a urea synthesis section and a urea concentration section.

BACKGROUND OF THE INVENTION

Urea ($NH_2CONH_2$) can be produced from ammonia and carbon dioxide at elevated temperature (typically between 150° C. and 250° C.) and pressure (typically between 12 and 40 MPa) in the synthesis zone of a urea plant. In this synthesis, two consecutive reaction steps can be considered to take place. In the first step ammonium carbamate is formed, and in the next step, this ammonium carbamate is dehydrated so as to give urea, The first step (i) is exothermic, and the second step can be represented as an endothermic equilibrium reaction (ii):

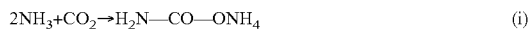

$$2NH_3 + CO_2 \rightarrow H_2N{-}CO{-}ONH_4 \quad (i)$$

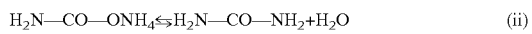

$$H_2N{-}CO{-}ONH_4 \leftrightarrows H_2N{-}CO{-}NH_2 + H_2O \quad (ii)$$

In a typical urea production plant, the foregoing reactions are conducted in a urea synthesis section so as to result in an aqueous solution comprising urea. In one or more subsequent concentration sections, this solution is concentrated to eventually yield urea in a form of a melt rather than a solution. This melt is further subjected to one or more finishing steps, such as prilling, granulation, pelletizing or compacting.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section followed by one or more recovery sections. The synthesis section comprises, a reactor, a stripper, a condenser and but not necessarily, a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide, inert gases and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor comprising non-condensed ammonia and carbon dioxide is sent to a scrubbing section operating at a similar pressure as the reactor. In that scrubbing section the ammonia and carbon dioxide is scrubbed from the inert vapor. The formed carbamate solution from the down stream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 0.2 to 0.5 MPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution. The vapor released in the heater of the recovery system comprises ammonia, carbon dioxide and water. Said vapor is condensed in a condenser. The heat of condensation is dissipated in cooling water. The formed carbamate is used as absorbent in said scrubber in the synthesis section. Some non-condensed vapor comprising ammonia, carbon dioxide and inert leaving that scrubber is sent to a condenser or absorber in order to purify the inert before releasing it into the atmosphere. The pressure in said condenser and/or absorber is typically lower than the pressure in the synthesis section.

An inherent consequence of the production of urea, is the unwanted emission of ammonia, particularly as a result of unreacted ammonia leaving the synthesis zone. Also in the most modern urea plants, this emission cannot be avoided, save for a prohibitive energy input and ditto operating costs to separate and capture all of the ammonia.

E.g., in a typical urea melt plant according the $CO_2$ stripping process, continuous ammonia emissions take place on the following process emission points:

low pressure absorber;
atmospheric absorber;
breathing system of the urea solution storage;
breathing system of the process condensate storage Thus, at several instance of the production of a urea melt, ammonia emissions occur. Whilst some may be discontinuous, a focus is on further reducing, and preferably avoiding, the continuous ammonia emissions.

The state of the art technology to minimize ammonia emissions from urea melt plants, is based on the "end-of-pipe" technology of "flaring". Especially for continuous ammonia emission reduction, flaring is a costly solution since flaring of these continuous emission sources requires relative large amounts of support gas and nitrogen to prevent explosive vapor mixtures caused by oxygen ingress via the flare tips. Besides, flaring gives a secondary emission by, e.g., nitrogen oxygen ($NO_x$) formation.

SUMMARY OF THE INVENTION

In order to better address one or more of the above desires, the invention, in one aspect, presents a method for the production of urea comprising subjecting ammonia and carbon dioxide to reaction under urea-forming conditions, so as to form an aqueous urea solution, subjecting said solution to concentration so as to form concentrated urea, the method comprising making available a gas stream comprising hydrogen gas, and subjecting said hydrogen-comprising gas to combustion, under the influence of oxygen, together with ammonia-comprising gas resulting from the urea production.

In another aspect, the invention provides the use, in the production of urea, of a synthesis section where the hydrogen is not combusted in the carbon dioxide feed to the synthesis, for the purpose of reducing the continuous emission of ammonia from a plant for the production of a urea melt, wherein urea is produced by subjecting, in said synthesis section, ammonia and carbon dioxide to reaction under urea-forming conditions, so as to form an aqueous urea solution, and subjecting said solution to concentration so as to form concentrated urea, wherein gas comprising hydrogen, gas comprising ammonia, and oxygen, are subjected to combustion.

In yet another aspect, the invention pertains to a plant for the production of urea, said plant comprising a urea synthesis section and an incinerator, said synthesis section comprising an outlet for liquid and an outlet for gas, said outlet for gas being, directly or indirectly, connected to a fuel inlet of the incinerator.

DETAILED DESCRIPTION OF THE INVENTION

Figure 1:
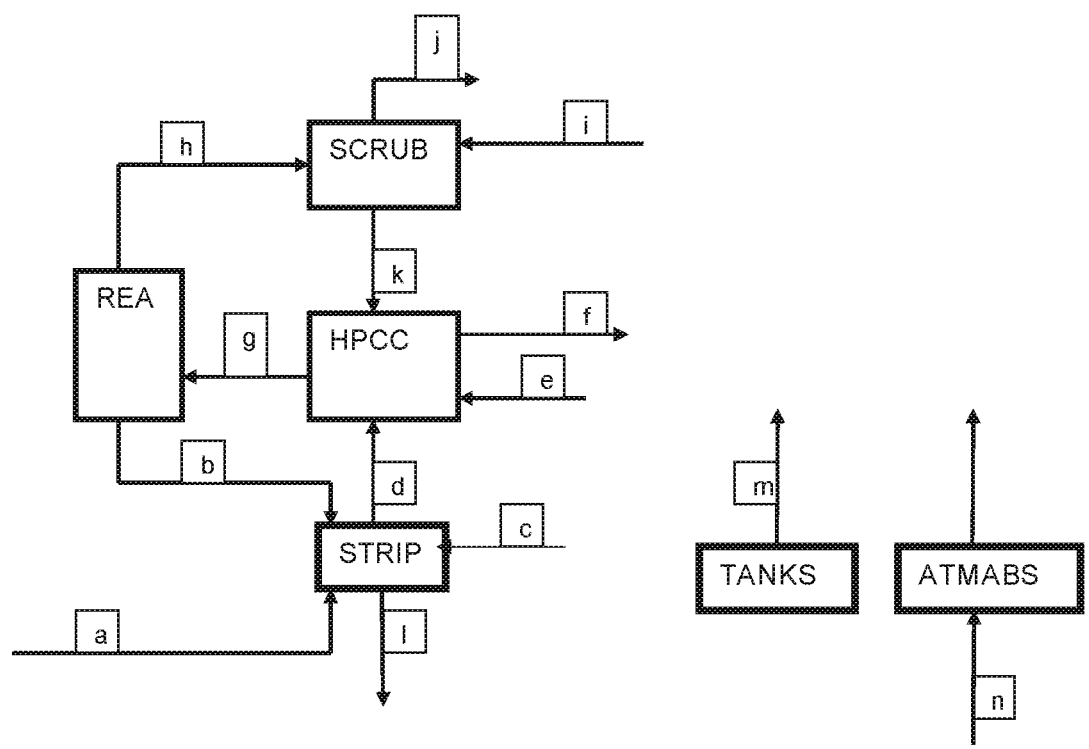
FIG. 1 is a schematic drawing of a conventional urea production plant of the $CO_2$ stripping type.

In the industrial starting chemicals for urea synthesis, notably in the carbon dioxide, hydrogen ($H_2$) is present as an impurity. Usually the amount of hydrogen in the carbon dioxide feed to the synthesis section of the urea plant amounts in between 0.05 and 1.2% by volume. In many urea production processes, this hydrogen is combusted, in the presence of oxygen, under the formation of water. To the extent that hydrogen may still be retained in a urea production process, this will normally be vented into the atmosphere, preferably early in the process.

The invention, in a broad sense, is based on the recognition that, in a urea production process, the hydrogen can be rendered useful as a fuel for the combustion of ammonia-comprising gas, for the purpose of reducing the continuous emissions of ammonia.

In order to realize this, it will be understood by the skilled person that the hydrogen-comprising gas is to be retained rather than vented, and it is to remain available as a fuel.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

In a preferred embodiment of the invention, the non-combustion conditions refer to the reduction, and preferable the absence, of oxygen in the synthesis section of the urea production plant. To this end it is preferred according to the invention to make use of a synthesis section made from material that does not necessarily require passivation by oxygen. Accordingly, the presence of oxygen in the reactor can be substantially avoided, e.g. up to 0.05 vol. % of the $CO_2$ feed used in the urea synthesis, and can even be zero.

In the presence of the passivation oxygen, the hydrogen will generally be prone to combustion under the formation of water. As a result of the substantial absence of oxygen, the hydrogen is essentially retained, and thus still available for further use. The same holds for methane ($CH_4$) that sometimes is also present in the carbon dioxide feed, and which is also an inert gas in respect of urea synthesis. The amount of hydrogen, and optionally methane, so made available is relatively high. E.g., a typical stream of inert gases from the urea synthesis after an absorption treatment comprises 70% by volume $H_2$, 20% by volume $CH_4$, and 10% by volume $N_2$.

The invention is based on the judicious insight that such available hydrogen, and optionally methane, can be used as a fuel in an incinerator, and that a benefit thereof is to burn $NH_3$-comprising gas streams in such an incinerator. It will be understood that in the incinerator oxygen needs to be present as well. This can be provided by the oxygen that will inherently be present in one or more of the $NH_3$-comprising vented gas streams, by separate addition of oxygen or air to the incinerator, or both.

In one preferred embodiment, on the basis of a material that does not require passivation by oxygen if used in the synthesis section of a urea production plant, said synthesis section comprises a duplex ferritic-austenitic stainless steel having a high content of Cr and N, and a low content of Ni. A reference in this respect is WO 95/00674, the disclosure of which is incorporated by reference herein. It will be understood, that other synthesis sections are conceivable, that can be used without passivation by oxygen. It will also be understood that the expression "made from" does not imply that each and every part of the synthesis section is made from said steel. Essentially, the parts in contact with the process fluid and thus inner parts which are exposed to the extremely corrosive circumstances of urea production, will be made of the aforementioned steel. Preferably, the entire reactor vessel consists essentially of such steel.

In another preferred embodiment, the synthesis section (and particularly the inner parts thereof) are made of a duplex stainless steel consisting of, in percent by weight, C: 0.03% or less, Si: 0.5% or less, Mn: 2% or less, P: 0.04% or less, S: 0.003% or less, Cr: 26% or more, but less than 28%, Ni: 7.3-10%, Mo: 0.2-1.7%, W: more than 2%, but no more than 3%, N: more than 0.3%, but no more than 0.4%, with the balance being Fe and impurities, in which the content of Cu as an impurity is not more than 0.1%. This steel is described in U.S. Pat. No. 7,347,903, the disclosure of which is incorporated by reference into this description.

The preferred synthesis section is made from a duplex, stainless steel alloy, containing, in percent by weight:
C: maximally 0.05%, preferably maximally 0.03%;
Si maximally 0.8%, preferably maximally 0.5;
Mn 0.3-4%, preferably 0.3-1%;
Cr 28-35%, preferably 29-33%;
Ni 3-10%;
Mo 1.0-4.0%, preferably 1.0-1.3%;
N 0.2-0.6%, preferably 0.36-0.55%;
Cu maximally 1.0%;
W maximally 2.0%;
S maximally 0.01%;
Ce 0-0.2%;
the remainder being Fe and normally occurring impurities and additives, the ferrite content being 30-70% by volume, preferably 33-35% by volume.

In the synthesis zone, ammonia and carbon dioxide are brought together at a suitable pressure (e.g. 12-40 MPa) and a suitable temperature (e.g. 150-250° C.), so as to allow the formation of ammonium carbamate, and subsequent dehydration to form urea. The urea is formed in an aqueous solution, and the off-gas of the synthesis zone comprises minor amounts of unreacted ammonia and carbon dioxide, and mostly the above-mentioned inert gases that were introduced as components in the starting material, and which are purged from the synthesis section to an absorption that is operating at a lower pressure than the synthesis pressure.

By virtue of the absence of a hydrogen combustion in the carbon dioxide feed and/or total absence of passivation oxygen in the reactor operated according to the process of the invention, the off-gas of the synthesis zone retains available hydrogen, and can be considered to be a relatively $H_2$-rich gas stream. Typically, the components in this stream will be within the following ranges expressed in percentages by volume:
unreacted $NH_3$: 0.1 to 10%;
unreacted $CO_2$: 0.1 to 10%;
hydrogen ($H_2$): 10 to 90%;
methane ($CH_4$): 0 to 20%;
nitrogen ($N_2$): 0 to 20%;

In conventional total recycle urea processes and urea processes according the urea stripping, the purge gas may still contain oxygen in addition to hydrogen, thus rendering this gas stream potentially inflammable. Conventional total recycle urea processes are characterized by the process conditions whereas the pressure in the synthesis is in between 19 and 22 MPa and the synthesis temperature is in between 185 and 210° C. In general the synthesis section in conventional total recycle urea plants consists of a reactor and on certain conventional urea synthesis sections a mixing vessel can be installed upstream of the reactor.

In such processes, the formed oxygen containing inert gas is therefore normally directly vented into the atmosphere. In the process of the invention, a hydrogen-rich gas stream results that is a fuel, but will not as such be inflammable. In order to burn the fuel gas as a fuel, it will be understood that further oxygen is needed.

According to the invention, this process is essentially used to burn $NH_3$ from the source itself and from one or more sources in the urea plant where other continuous inert vapour comprising ammonia are vented such as breathing gases of tanks and inert gases leaving absorbers and/or condensers. Thus, one or more gas streams comprising $NH_3$ are fed into an incinerator and burned therein with the hydrogen-rich stream made available as a fuel, and oxygen and/or air made available to enable the burning.

The sources of the air and/or oxygen can be manifold. E.g., it can be provided separately (via an air-inlet) in the incinerator that is used for burning the hydrogen-rich stream. Preferably, however, at least part of the air and/or oxygen will be harvested from one or more other gas sources in the same urea plant, and/or in any plant that might be coupled with the urea plant. These air and/or oxygen sources may contain small amounts of ammonia.

Thus, the hydrogen-rich stream from the synthesis zone is preferably combined with one or more air and/or oxygen-rich streams into an incinerator.

The air and/or oxygen-rich streams can be the same gas streams as the ammonia-comprising streams to be burned i.e. from breathing systems of tanks and absorbers.

The urea plant can further be any type of urea plant. An overview of commercial processes for producing urea is given, e.g., in Ullmann Encyclopedia, 2005 Wiley-VCH Verlag, Weinheim, Germany, chapter "Urea."

The invention adds, as a separate unit or as an integral part of the plant, an incinerator. Any incinerator capable of receiving, retaining, and burning gases can be used. The burning (combustion) will take place in a combustion chamber. The burning is fuelled by the aforementioned hydrogen-rich stream of the urea plant. It is conceivable to supply spare fuel, for use in circumstances where incineration is desired whilst, for any reason as may occur in the daily practice of an industrial plant, the retrieval or availability of hydrogen from the synthesis zone might have been disturbed.

Incinerators, suitable burners, and combustion chambers are known to the skilled person, and do not require specific elucidation here. In the combustion chamber of the incinerator the combustion takes place. As is customary, a pilot light supported by natural gas can be present.

The vapor leaving the incineration chamber is preferably cooled down by generating steam and thereafter sent into the atmosphere, via a catalyst for selective catalytic reduction (SCR catalyst) so as to reduce any $NO_x$ emissions. A small portion of ammonia and/or urea solution is added to the SCR catalyst for the reduction reaction of $NO_x$ in the exhaust of the incinerator, formed as a result of the high temperatures in the incineration chamber. Systems to control the reduction reaction are customary in the art, and commercially available.

The generated steam is introduced into the steam system of the urea melt plant and advantageously decreases the high-pressure steam consumption of the plant. Generally the steam saving of the urea plant decreases by typical about 10 to 50 kg/ton extraction steam by this application dependent of the hydrogen content in the $CO_2$ feedstock and the efficiency of the heat recovery system of the incinerator.

Alternatively, the vapor leaving the incineration chamber can be subjected to selective non catalytic reduction (SNCR) in order to thermally reduce the formed NOx and subsequently to selective catalytic reduction (SCR). In this way more than 90% of the NOx present in the gases leaving the incinerator can be removed, and the remaining ammonia does not exceed a few ppm. The thermal denox or SNCR is a post-combustion reduction method that reduces NOx through a controlled injection of reducing component into the combustion gas. The reducing component, or reductor, in SNCR, SCR, or both can be ammonia or urea preferably supplied from the urea plant. More preferably, the reducing component is ammonia. The operating temperature is at about 950-1100° C., therefore preferably quench air is sent to reduce the flue gas temperature. Hence, in this embodiment, the cooling of the gas stream takes place after the SNCR and, optionally, also after the SCR. In this latter case, the flue gases from the SCR catalyst are used to preheat boiler feed water to rise steam to be used elsewhere in the system, e.g. as heating agent. In order to improve mixing, the incinerator can be provided with a throat device.

The invention also adds to conventional total recycle urea plants and stripping plants where the hydrogen in the carbon dioxide feed to the synthesis section is not combusted the necessary flow lines to be able to retrieve the aforementioned hydrogen-rich stream from the synthesis section, and to feed this stream into the incinerator. The invention also adds to conventional total recycle urea plants, the necessary flow lines to send one or more $NH_3$-comprising streams from the urea production process to the incinerator i.e from breathing systems and absorbers.

The invention also pertains to a plant for the production of urea, said plant comprising a urea synthesis section and an incinerator, said synthesis section comprising an outlet for liquid and an outlet for gas, said outlet for gas being, directly or indirectly, connected to a fuel inlet of the incinerator.

In its most simple form, the plant of the invention comprises a reactor for conducting the reaction between ammonia and carbon dioxide, under the formation of urea as indicated above. The reactor will have, as conventional, outlets for the formed urea solution (i.e. the outlet for liquid) and for the remaining gas (ammonia, carbon dioxide, and inerts). As a novelty according to the invention, the gas outlet is directly or indirectly (i.e. irrespective of any further treatment steps) connected to the burners of an incinerator.

Preferably, the synthesis section comprises, in addition to the reactor, a stripper, a condenser, and a scrubber, as is conventional in a urea stripping plant. In this embodiment, the aforementioned gas outlet of this synthesis section is connected, directly or indirectly, to the incinerator. Preferably, an absorber is foreseen between the synthesis section and the incinerator.

The plant according to the invention provides the possibility to employ fuel-containing gas retrieved from the urea synthesis section, as a fuel in the incinerator. Therewith the plant can be tuned to result in a reduction of the continuous emission of ammonia, by combusting ammonia-comprising gas in said incinerator. To this end, in a preferred embodiment, the plant of the invention comprises an incinerator the combustion chamber of which comprises a gas inlet being connected from a unit that serves as a source of ammonia-comprising gas such as breathing gases of tanks and remaining inert gases from atmospheric absorbers.

In another aspect, the invention is based on the judicious insight that the choice of the aforementioned type of synthesis section that does not require substantial passivation by oxygen, enable serving the purpose of reducing the continuous emission of ammonia from a plant for the production of a urea melt. This purpose is achieved as described hereinbefore. Therein urea is produced by subjecting, in said synthesis section, ammonia and carbon dioxide to reaction under urea-forming conditions, so as to form an aqueous urea solution, and subjecting said solution to concentration so as to form concentrated urea, wherein gas comprising hydrogen, gas comprising ammonia, and oxygen, are subjected to combustion.

By virtue of the invention, a substantial reduction, even down to zero, of the continuous emission of ammonia conventionally resulting from the production of urea can be achieved.

The invention will hereinafter be further illustrated with reference to the following, non-limiting examples.

Example 1

In this example the prior art of a typical urea stripping synthesis section is described and illustrated in the FIG. 1.

Carbon dioxide is added to the stripper (STRIP) via line (a) in the urea synthesis section of the urea stripping process. The carbon dioxide contains inerts and hydrogen and sometimes methane and may comprise air for keeping the fabrication materials of the equipment and lines in that synthesis section resistant against excessive corrosion. In some urea synthesis sections, the hydrogen in the carbon dioxide is combusted before arriving into the synthesis section. Urea solution from the reactor (REA) is supplied to the stripper (STRIP) via line (b) and is counter currently contacting the supplied carbon dioxide. By this the partial pressure of ammonia in the urea solution is decreased and makes the non converted carbamate to decompose. As a heating agent, steam at a typical pressure of 1.5 to 2.5 MPa is supplied to the shell side of said stripper (STRIP) via line (c) in order to obtain a urea concentration in the urea solution leaving that stripper of approximately 45 to 56% by weight via line (l). The vapor leaving the stripper (STRIP) via line (d) contains ammonia, carbon dioxide, inert and a small amount of water and is supplied to a condenser (HPCC). Ammonia is supplied to that condenser (HPCC) as well via line (e). In this condenser the ammonia and carbon dioxide is condensed into a carbamate solution. The released condensation heat is used to produce steam via line (f) that is used for heating purposes in the downstream processing of the urea plant. If the condenser (HPCC) is a submerged type, residence time of the liquid phase is created and that makes that the endothermic urea reaction proceeds. The formed solution together with non condensed inert vapor leaving the condenser (HPCC) is sent to the reactor (REA) via line (g) where the endothermic urea reaction approaches the equilibrium. In the top of the reactor (REA) the solution is separated from the non-condensed inert vapor. The solution is sent to said stripper (STRIP) via line (b) and the non-condensed inert vapor is sent to the scrubber (SCRUB) via line (h). In the scrubber (SCRUB) the non-condensed ammonia and carbon dioxide is separated from the inert vapor by using the formed carbamate in the downstream recovery section as absorbent via line (i). The inert vapor via line (j) is sent into the atmosphere directly or can be treated in one or more absorbers operated at a lower pressure than the pressure in the synthesis section. Typically the ammonia released by this vented vapor is 0.05 to 25 kg per produced ton of urea. The formed carbamate solution in the scrubber (SCRUB) is returned to the condenser (HPCC) via line (k).

In the downstream processing of the urea synthesis section inert vapor that contains ammonia is released into the atmosphere. The source of this vented vapor comes from e.g. breathing systems of tanks via line (m) and/or vacuum systems to concentrate the urea solution via line (n). These vapors can but not necessarily need to be treated in one or more absorbers (ATMABS) before releasing into the atmosphere. Typically the ammonia released by these vented vapors is 0.01 to 20 kg per produced ton of urea.

Example 2

Figure 2:
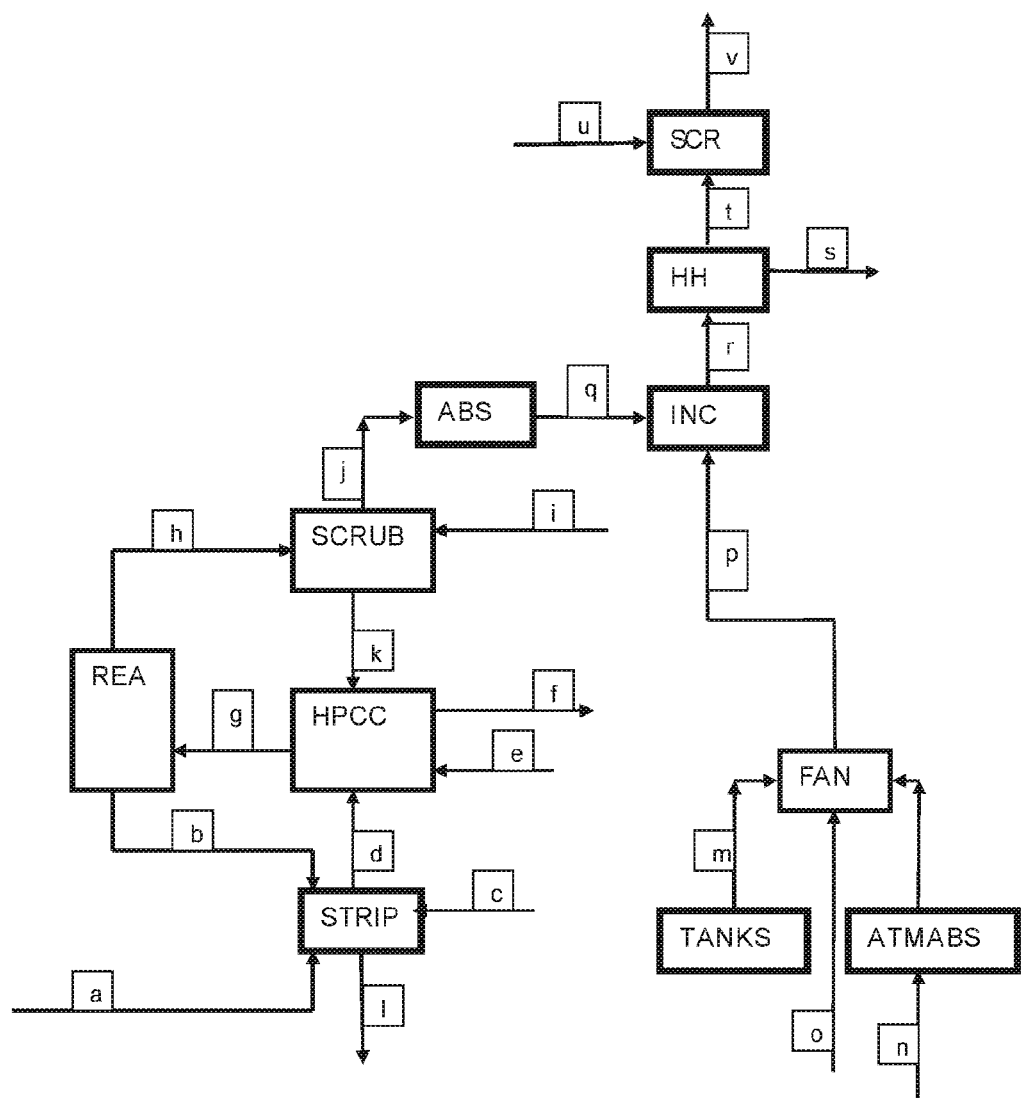
FIG. 2 is a schematic drawing of a urea production plant, of the $CO_2$ stripping type, in accordance with the invention.

This example, with reference to FIG. 2, illustrates an example according the invention. The synthesis section is made of duplex stainless steel in accordance with WO 95/00674.

Carbon dioxide is added to the stripper (STRIP) via line (a) in the urea synthesis section of the urea stripping process. The carbon dioxide contain inert and hydrogen. Urea solution from the reactor (REA) is supplied to the stripper (STRIP) via line (b) and is counter currently contacting the supplied carbon dioxide. By this the partial pressure of ammonia in the urea solution is decreased and makes the non converted carbamate to decompose. As a heating agent, steam at a typical pressure of 1.5 to 2.5 MPa is supplied to the shell side of said stripper (STRIP) via line (c) in order to obtain a urea concentration in the urea solution leaving that stripper of approximately 45 to 56% by weight. The vapor leaving the stripper (STRIP) via line (d) contains ammonia, carbon dioxide, hydrogen, optionally methane, inert and a small amount of water and is supplied to a condenser (HPCC). Ammonia is supplied to that condenser (HPCC) as well via line (e). In this condenser the ammonia and carbon dioxide is condensed into a carbamate solution. The released condensation heat is used to produce steam via line (f) that is used for heating purposes in the downstream processing of the urea plant. If the condenser (HPCC) is a submerged type, residence time of the liquid phase is created and that makes that the endothermic urea reaction proceeds. The formed solution together with non condensed inert vapor leaving the condenser (HPCC) is sent to the reactor (REA) via line (g) where the endothermic urea reaction approaches the equilibrium. In the top of the reactor (REA) the solution is separated from the non-condensed inert vapor. The solution is sent to said stripper (STRIP) via line (b) and the non-condensed inert vapor is sent to the scrubber (SCRUB) via line (h). In the scrubber (SCRUB) the non-condensed ammonia and carbon dioxide is separated from the inert vapor that contains among non-condensed ammonia and carbon dioxide also hydrogen by using the formed carbamate in the downstream recovery section as absorbent via line (i). The inert vapor comprising hydrogen and possibly (but not necessarily) methane via line (j) is sent into an absorber (ABS) that operates at a lower pressure than the pressure in the synthesis section. The formed carbamate solution in the scrubber (SCRUB) is returned to the condenser (HPCC) via line (k). The hydrogen comprising inert vapor leaving the absorber (ABS) via line (q), is subjected to the burners of the incinerator (INC).

In the downstream processing of the urea synthesis section inert vapor that contains ammonia is released into the combustion chamber of the incinerator (INC). The source of this vented vapor comes from i.e. breathing systems of tanks via line (m) and/or vacuum systems to concentrate the urea solution via line (n). These vapors can be treated, but not necessarily so, in one or more absorbers (ATMABS). The air containing vented vapors are collected via line (p) and by addition of air via line (o) these gas mixtures are subjected to the combustion chamber of the incinerator (INC). In case atmospheric tanks or absorbers are involved, these vapors may be increased in pressure via a fan (FAN) to overcome the necessary pressure drop of the incinerator (INC) and involved lines. The operating pressure in the incinerator is maximum the pressure of the hydrogen comprising vapor and minimum atmospheric. In the incinerator (INC) the combustion of hydrogen and air takes place. The required air containing vented vapor is in excess compared to the hydrogen comprising vapor in order to ensure complete hydrogen combustion. By the existing high temperature of that hydrogen combustion reaction, all the ammonia arriving from any source in the incinerator (INC) is combusted.

The hot vapor leaving the incinerator comprises $NO_x$ and is cooled down in a heat exchanger (HH) by producing steam at a pressure in between 0.4 and 2.5 MPa via line (s). The amount of produced steam is typically in between 2 and 50 kg per ton of produced urea dependent of the amount of hydrogen in the carbon dioxide feedstock to the synthesis section as expressed by line (a). The produced steam can be used as heating agent in the urea plant itself or can be exported to process facilities outside the urea plant. The released cooled vent gases from the heat exchanger (HH) is subjected by line (t) to a SCR catalyst (SCR) where the $NO_x$, present in that vapor is reduced to nitrogen and water. As a reductor, ammonia or urea can be used and that is added via line (u) to that catalyst (SCR).

The ammonia and the $NO_x$ in the vented vapor leaving the catalyst (SCR) via line (v) is negligible (≤0.01 kg per ton of produced urea) and is vented into the atmosphere.

In an alternative embodiment (not shown in FIG. 2), the hot vapor leaving the incinerator (INC) is further sent to a thermal denox unit operating at 1100° C. wherein NOx is reduced through a controlled injection of reducing component into the combustion gas. The reducing component is ammonia that is supplied from the urea plant. In order to reach the operating temperature of 350° C. at the entry of catalytic denox, a quench boiler is placed downstream of the thermal denox step that cools down the gas leaving the thermal denox unit. The quench boiler produces steam that can be used as heating agent in the urea plant. The cooled gas stream is further sent to a catalytic denox unit, or SCR (Selective Catalytic Reduction). During the SCR the NOx present in the gas stream react with gaseous ammonia from the urea plant in the presence of a catalyst to reduce under the appropriate conditions to produce nitrogen and water. Optionally, a heat exchanger for a further recovery of heat and for the reduction of the temperature of the flue gases, could be included after the SCR step. In the resulting stream obtained in this embodiment, upto 90% of the NOx and preferably even more are removed from the gas stream and the ammonia content is less than few ppm.

The invention claimed is:

1. A method for the production of urea in a plant for the production of urea, the plant comprising a urea synthesis section, wherein the urea synthesis section has an outlet for urea solution and an outlet for gas, and wherein the plant further comprises an incinerator and downstream of said outlet for urea solution one or more downstream processing units, the method comprising
    subjecting ammonia and a feed comprising carbon dioxide and hydrogen to reaction under urea-forming conditions in said urea synthesis section in the absence of oxygen, so as to form an aqueous urea solution, supplying gas comprising hydrogen from said outlet for gas of said urea synthesis section to said incinerator, and subjecting said aqueous urea solution to concentration so as to form concentrated urea in said one or more downstream processing units, wherein in at least one of said one or more downstream processing units, inert vapor that contains ammonia is released, supplying said inert vapor that contains ammonia from one or more of said downstream processing units to said incinerator, and subjecting in said incinerator said gas comprising hydrogen to combustion, together with said inert vapor that contains ammonia from one or more of said downstream processing units in the presence of oxygen.

2. A method according to claim 1, wherein said gas stream is directed to the combustion chamber of an incinerator and are used for the combustion of the gas stream comprising hydrogen.

3. A method according to claim 2, wherein air is added to the combustion chamber of the incinerator.

4. A method according to claim 3, wherein the generated heat of combustion is used to produce steam at a pressure between 0.3 and 3 MPa.

5. A method according to claim 2, wherein vapor generated in the incinerator is subjected to an SCR catalyst in order to reduce the formed NOx.

6. A method according to claim 5, wherein, prior to SCR, the vapor is subjected to a selective non-catalytic reduction (SNCR).

7. A method according to claim 1, wherein the reaction between ammonia and carbon dioxide is conducted in a synthesis section made from a duplex ferritic-austenitic stainless steel having a content of Cr of at least 28 wt % and N of at least 0.2 wt %, and a content of Ni of no more than 10 wt %.

8. A method according to claim 7, wherein the synthesis section is made from a duplex, stainless steel alloy, containing, in percent by weight:
C maximally 0.05%;
Si maximally 0.8%;
Mn 0.3-4%;
Cr 28-35%;
Ni 3-10%;
Mo 1.0-4.0%;
N 0.2-0.6%;
Cu maximally 1.0%;
W maximally 2.0%;
S maximally 0.01%;
Ce 0-0.2%;
the remainder being Fe and normally occurring impurities and additives, the ferrite content being 30-70% by volume.

9. A method according to claim 1, wherein the feed comprising hydrogen gas also comprises methane gas.

10. A method for reducing the continuous emission of ammonia from a plant for the production of a urea melt, wherein the plant comprises a urea synthesis section, wherein the urea synthesis section has an outlet for urea solution and an outlet for gas, and wherein the plant further comprises an incinerator and downstream of said outlet for urea solution one or more downstream processing units in which said urea solution is subjected to concentration so as to form concentrated urea and inert vapor that contains ammonia is released, wherein in said plant urea is produced by subjecting, in said urea synthesis section, ammonia and a feed containing carbon dioxide and hydrogen to reaction under urea-forming conditions so as to form an aqueous urea solution without substantial combustion of said hydrogen contained in said carbon dioxide feed;

said method comprising supplying hydrogen-containing gas from said outlet for gas to said incinerator, supplying said inert vapor that contains ammonia to said incinerator, and subjecting said hydrogen-containing gas and inert vapor that contains ammonia to combustion in said incinerator together with oxygen or air.

11. A method according to claim 10, wherein the synthesis section is made of a duplex ferritic-austenitic stainless steel having a content of Cr of at least 28 wt % and N of at least 0.2 wt %, and a content of Ni of no more than 10 wt %.

12. A method according to claim 10, wherein the carbon dioxide feed and the effluent contain methane.

13. A method according to claim 1, wherein said gas comprising hydrogen is obtained from a urea reactor in said urea synthesis section, wherein urea is formed in said urea reactor.

14. A method according to claim 1, wherein said ammonia is obtained from one or more of said downstream processing units, wherein said units are selected from the group consisting of an atmospheric absorber, a breathing system of urea storage and a breathing system of a process condensate storage.

15. A method according to claim 1, wherein the urea synthesis is conducted at 12-40 MPa and 150°-250° C. in a total recycle process.

* * * * *